(12) United States Patent
Bunner et al.

(10) Patent No.: US 9,409,252 B2
(45) Date of Patent: Aug. 9, 2016

(54) CHROMATOGRAPHY APPARATUS HAVING DIFFUSION-BONDED AND SURFACE-MODIFIED COMPONENTS

(75) Inventors: Bernard Bunner, Newton, MA (US);
Theodore A. Dourdeville, Providence, RI (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 882 days.

(21) Appl. No.: 13/637,273

(22) PCT Filed: Mar. 25, 2011

(86) PCT No.: PCT/US2011/029934
§ 371 (c)(1),
(2), (4) Date: Sep. 25, 2012

(87) PCT Pub. No.: WO2011/119922
PCT Pub. Date: Sep. 29, 2011

(65) Prior Publication Data
US 2013/0014567 A1    Jan. 17, 2013

Related U.S. Application Data

(60) Provisional application No. 61/317,767, filed on Mar. 26, 2010.

(51) Int. Cl.
*B23K 20/02* (2006.01)
*B01L 3/00* (2006.01)
(Continued)

(52) U.S. Cl.
CPC ......... *B23K 20/023* (2013.01); *B01L 3/502707* (2013.01); *B01L 3/502753* (2013.01);
(Continued)

(58) Field of Classification Search
CPC ............... B01L 2200/0689; B01L 2300/0816; B01L 2300/0887; B01L 2400/0487; B01L 3/502707; B23K 2201/18; B23K 2203/14; G01N 30/6095; G01N 30/7266; H01J 49/0018
See application file for complete search history.

(56) References Cited

U.S. PATENT DOCUMENTS 4,890,784 A    1/1990    Bampton
5,792,943 A    8/1998    Craig
(Continued)

FOREIGN PATENT DOCUMENTS

JP    2005-257544 A    9/2005
WO    WO 2008106613 A2 *    9/2008
(Continued)

OTHER PUBLICATIONS

International Search Report for related PCT Application No. PCT/US11/29934, 3pp, May 17, 2011.
(Continued)

*Primary Examiner* — Daniel S Larkin
*Assistant Examiner* — Jamar Ray
(74) *Attorney, Agent, or Firm* — McCarter & English, LLP; Deborah M. Vernon

(57) ABSTRACT

A microfluidic device for separating a sample by chromatography includes diffusion bonded metallic sheets joined together to create a hermetically sealed interface between each adjacent metallic sheet without the introduction of a secondary material. Enclosed within the diffusion bonded sheets is a separation channel accessible by at least one of an inlet or an outlet. The separation channel is packed with micrometer-sized particles serving as a stationary phase in a chromatographic separation. Wetted surfaces of the separation channel include a coating of an organic material at least one monolayer thick.

16 Claims, 10 Drawing Sheets

(51) Int. Cl.
*B23K 20/233* (2006.01)
*G01N 30/60* (2006.01)
*H01J 49/00* (2006.01)
*H01J 49/16* (2006.01)
*B23K 101/18* (2006.01)
*B23K 103/14* (2006.01)
*G01N 30/72* (2006.01)

(52) U.S. Cl.
CPC .......... *B23K20/233* (2013.01); *G01N 30/6095* (2013.01); *H01J 49/0018* (2013.01); *H01J 49/167* (2013.01); *B01L 2200/0689* (2013.01); *B01L 2300/0816* (2013.01); *B01L 2300/0887* (2013.01); *B01L 2400/0487* (2013.01); *B23K 2201/18* (2013.01); *B23K 2203/14* (2013.01); *G01N 30/7266* (2013.01)

(56) References Cited

U.S. PATENT DOCUMENTS

| | | | |
|---|---|---|---|
| 5,840,388 A * | 11/1998 | Karger | B01J 20/262 204/451 |
| 6,766,817 B2 | 7/2004 | da Silva | |
| 7,534,753 B2 | 5/2009 | Wu et al. | |
| 2003/0008411 A1 | 1/2003 | Van Dam et al. | |
| 2003/0061867 A1 | 4/2003 | Gerner et al. | |
| 2004/0238052 A1 | 12/2004 | Karp et al. | |
| 2005/0072671 A1* | 4/2005 | Rocklin et al. | 204/409 |
| 2006/0171654 A1 | 8/2006 | Hawkins et al. | |
| 2007/0077771 A1* | 4/2007 | Plissonnier et al. | 438/758 |
| 2009/0057375 A1 | 3/2009 | Crockett et al. | |
| 2009/0117664 A1* | 5/2009 | Shinoda | B01L 3/50273 436/172 |
| 2009/0282978 A1 | 11/2009 | Jensen et al. | |

FOREIGN PATENT DOCUMENTS

| | | |
|---|---|---|
| WO | WO-2008106613 A3 | 11/2008 |
| WO | 2008150482 A2 | 12/2008 |

OTHER PUBLICATIONS

Written Opinion for related PCT Application No. PCT/US11/29934, 6pp, May 17, 2011.

* cited by examiner

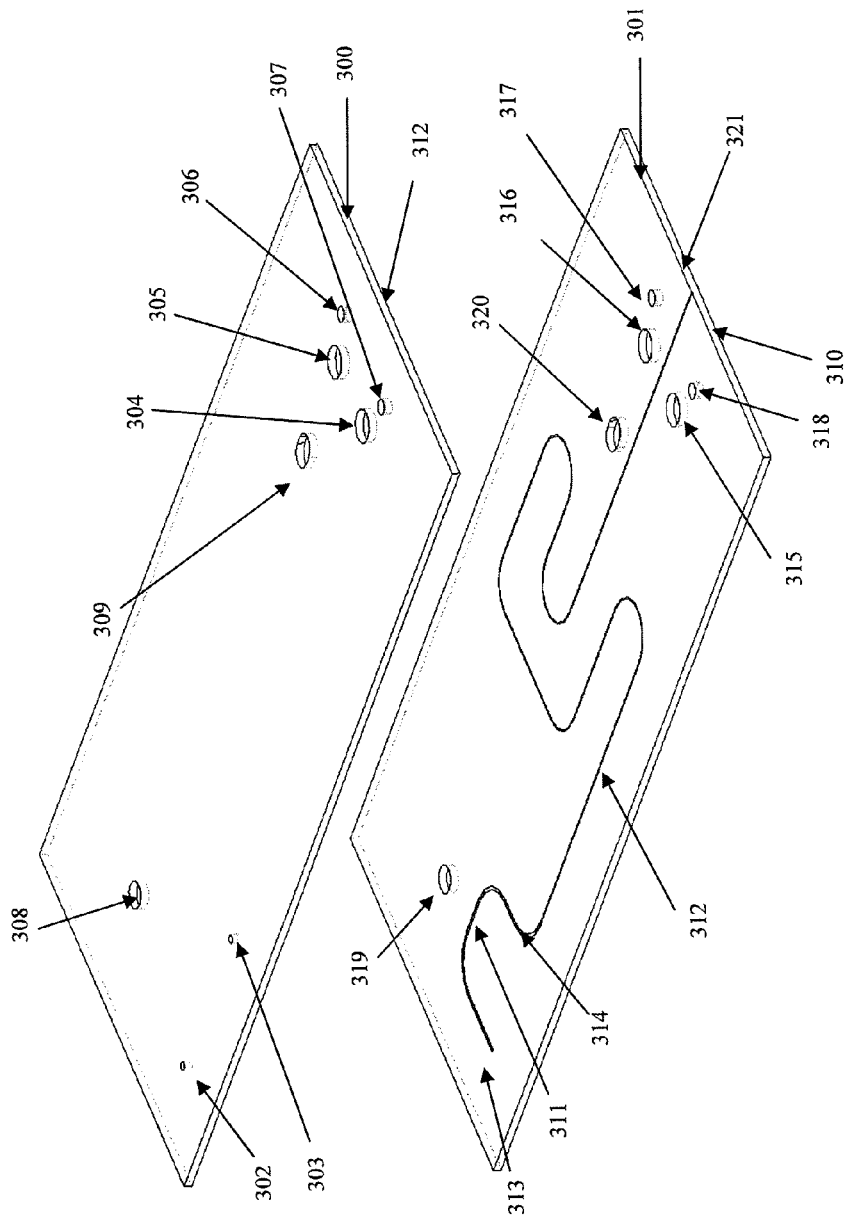

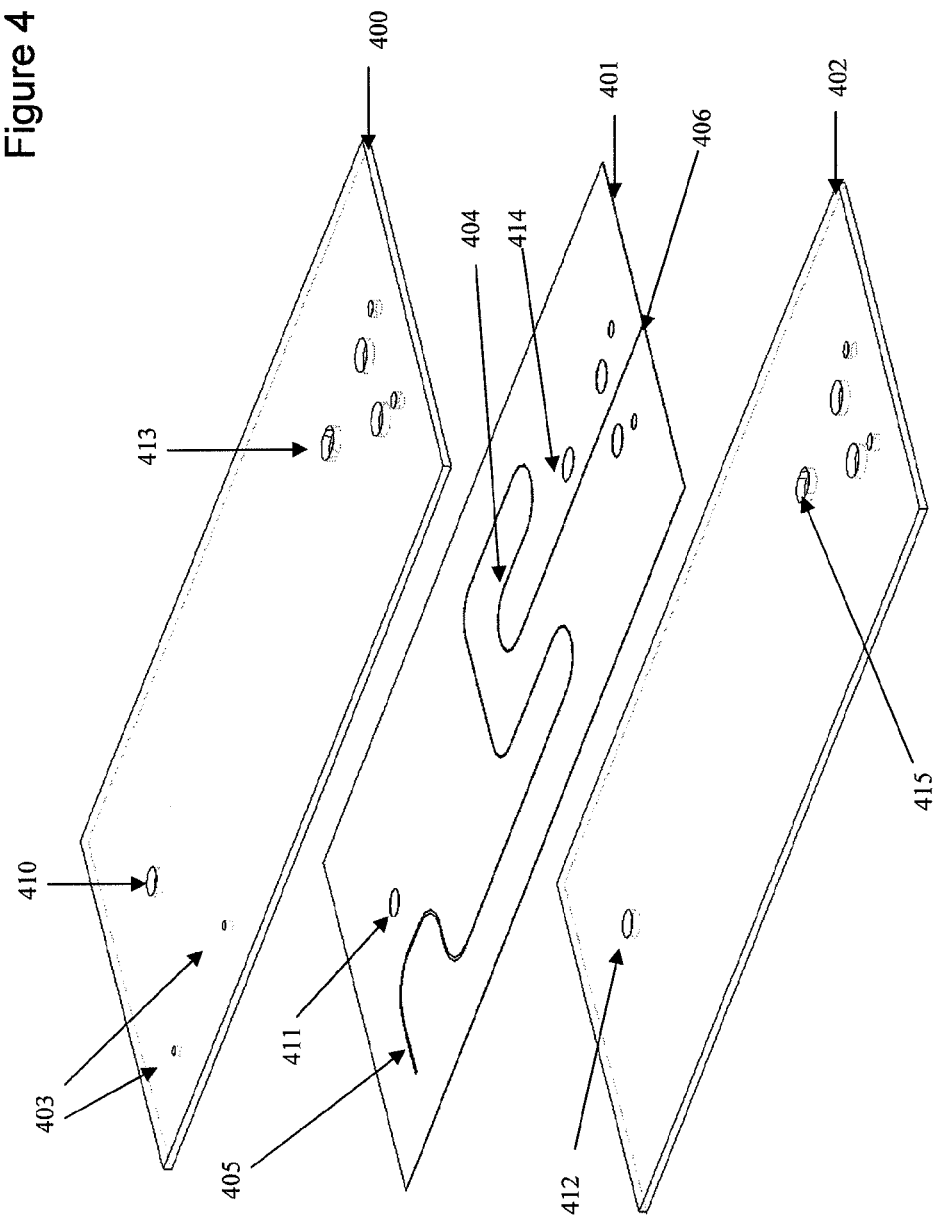

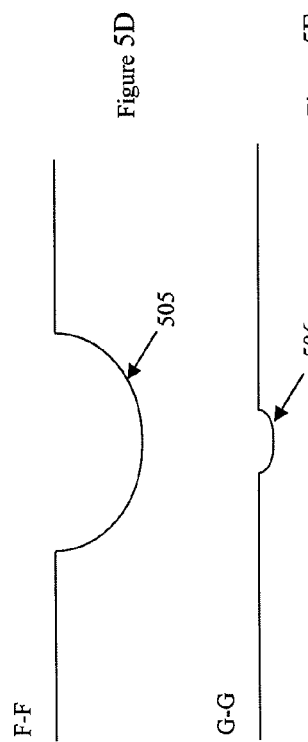
Figure 5D
Figure 5E
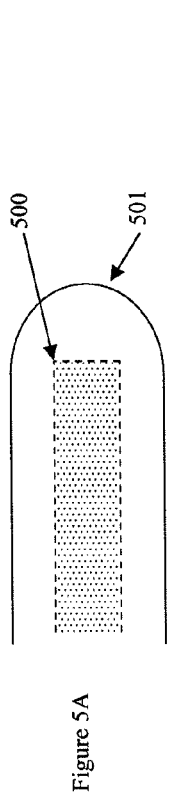
Figure 5A
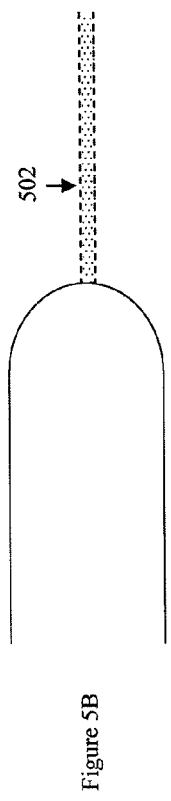
Figure 5B
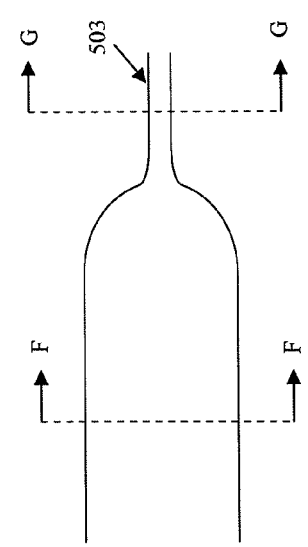
Figure 5C

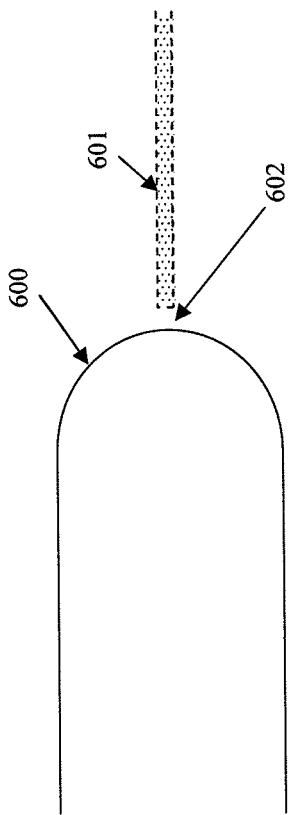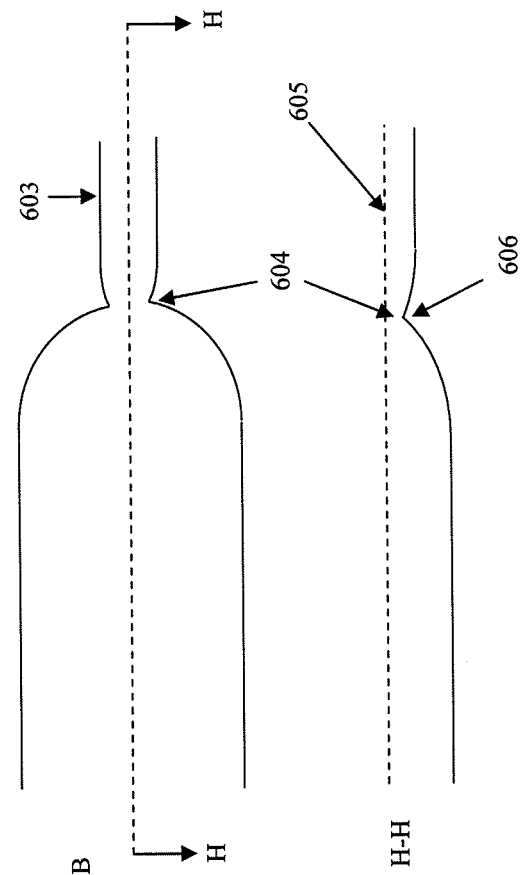
Figure 6A  Figure 6B  Figure 6C

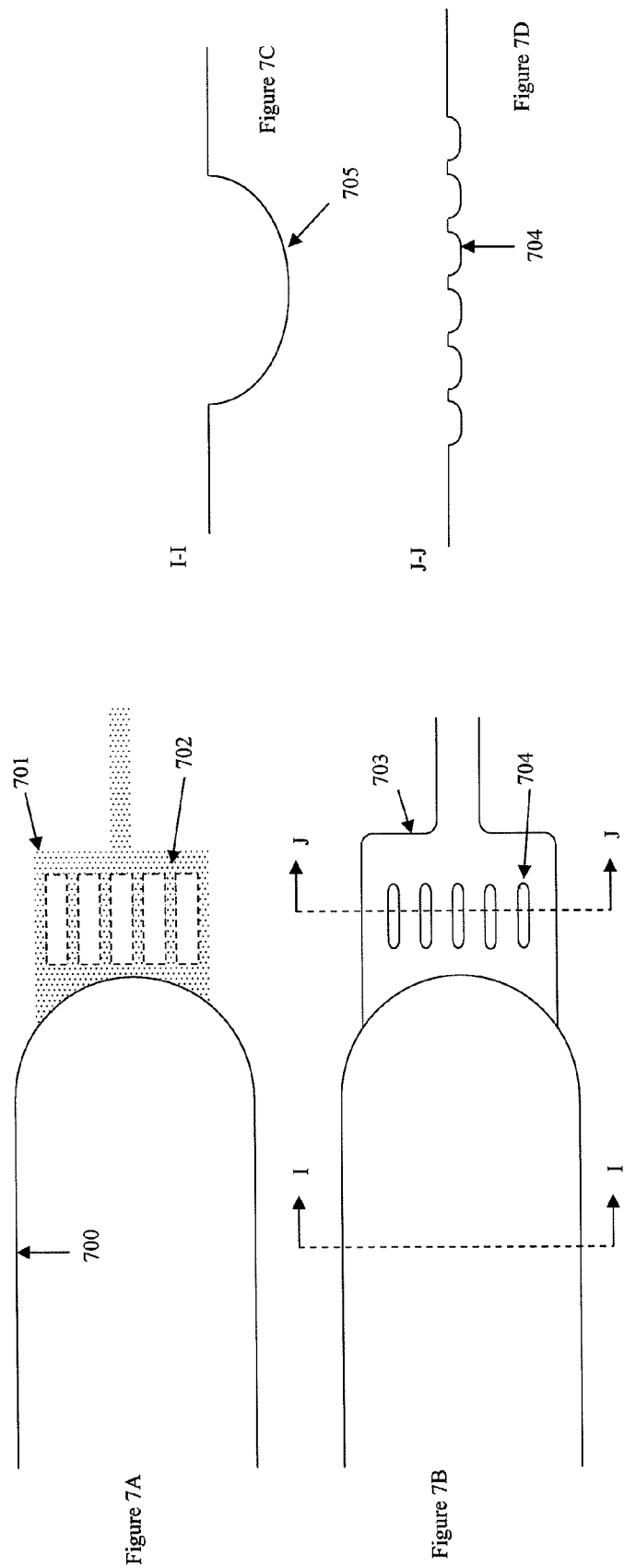

CHROMATOGRAPHY APPARATUS HAVING DIFFUSION-BONDED AND SURFACE-MODIFIED COMPONENTS

RELATED APPLICATIONS

This application is a National Stage Application of International Application Number PCT/US2011/029934, filed on Mar. 25, 2011, which claims the benefit of and priority to U.S. Provisional Application No. 61/317,767, filed Mar. 26, 2010, both of which are owned by the assignee of the instant application and the disclosures of which are hereby incorporated by reference in their entirety.

TECHNICAL FIELD

The technology generally relates to chromatography apparatus, and, in particular, high-pressure liquid-chromatography instruments.

BACKGROUND INFORMATION

A brief discussion of the volume-scale of chromatography and its effect on fluid-path implementation is given below. High-performance liquid chromatography (HPLC) is traditionally performed using analytical columns having a finished internal diameter (ID) or bore of about 4.6 millimeters, and a length typically in the range of about 5 centimeters to 25 centimeters. Such columns are typically assembled from carefully machined components.

The column tube typically has a male thread on each end, which engages a corresponding female thread within respective column end-fittings or terminals. Each column end-fitting incorporates features critical to the performance of the finished column. Among these features is a fit and diffuser plate, which cooperate to retain the particulate stationary phase (or packing) within the column bed, and to transition the liquid flow between the geometry of the narrow-bore input/output interconnect tubing (typically 0.23 millimeters ID) and the much broader diametral dimension of the packed bed (4.6 millimeters.) Each column end-fitting also includes a threaded compression port, which is used to establish a substantially leak-tight interface between the column and an interconnect tube.

A traditional 4.6 mm ID HPLC column might be packed with a stationary phase incorporating a characteristic packing-particle diameter of 5 micrometers. Operation of that column at a suitable mobile-phase volumetric flow rate will result in a characteristic mobile-phase linear velocity through the bed structure. If the column is well-packed (i.e. in the substantial absence of voids, bridges, or other bed defects) then this operating regime will result in a characteristic separation "efficiency" for this system, as demonstrated through the use of one or more types of probe compounds. The characteristic efficiency may be thought of as a measure of the narrowness of the chromatographic zones or bands which may be propagated through the system.

In an HPLC analytical instrument, it is generally desirable to perform separations with high efficiency, thereby maximizing information content of the chromatogram by enhancing the resolution of interfering or near-interfering zones or bands. A band which is eluted from the above-described system might be expected to have a time-course of substantially 10 seconds, measured at 5-sigma (i.e., passage of the substantially Gaussian concentration-distribution of the band through a detector, including the band apex, as well as 2.5-sigma of the band preceding and trailing the apex.)

With knowledge of the volumetric flow rate, one can convert the width of the band in time units to a width in volume units (167 microliters in this example, for a flow rate of 1.0 milliliter per minute. Working in the volume domain is particularly instructive as one proceeds to investigate the impact of "extra-column" volumes on the efficiency of the separation. The existence of volumes external to the column (for example, in transport tubing, in detectors, and in injectors) generally can only degrade the quality of a separation as delivered by a column.

The extra-column variance (variance=$sigma^2$) contribution is an extremely useful measure to illuminate how a specified separation will be degraded in the presence of one or more types of extra-column contributions, as variances are substantially additive. It is instructive to tabulate the characteristic volume scale of several classes of chromatography systems, to perceive what the system designer is confronted with. In the tabulation below, the assumption is made that all systems will preserve the same efficiency value, and that mobile-phase linear velocity will be maintained constant through the packed bed. Thus, the volumetric flow rate has been scaled in proportion to column bed cross-sectional area, thus in proportion to column internal $radius^2$.

TABLE 1

| HPLC Scale | Column ID | Volumetric Flow Rate | Characteristic Peak Volume |
|---|---|---|---|
| Conv. Analytical | 3.9-4.6 mm | 1.0 milliliter/min | 167-200 microliters |
| Narrow-bore | 2.0 mm | 250 microliters/min | 40-50 microliters |
| Microbore | 1.0 mm | 50-70 microliters/min | 10-12 microliters |
| Capillary | 0.30-0.50 mm | 5-12 microliters/min | 1.5-2.5 microliters |
| Nanoscale | 0.05-0.15 mm | 10's-100's nanoliters/min | 10-40 nanoliters |

It will be further recognized that as one transitions to the use of smaller appropriately-packed particles to construct the chromatography column bed, one can achieve higher separation efficiencies. This regime, as commercialized by Waters Corporation (Milford, Mass., USA) using nominal 1.7 micrometer diameter particles, has been termed Ultra Performance Liquid Chromatography™ (UPLC™). The bands or zones in UPLC™ are thus narrower (in both the time domain and the volume domain) than their counterparts in HPLC, placing further demands on reduction of extra-column volume and its zone-dispersion effects.

The column and flow-rate ranges of Table 1 illustrate how conventional tubing and tubing-interfaces, which are quite satisfactory for use in conventional-scale HPLC (where characteristic peak volumes are a significant fraction of a milliliter,) are quickly outclassed in applications such as capillary-scale or nanoscale HPLC (where characteristic peak volumes are in the few-microliter to tens-of-nanoliters range, and thus the extra-column variance "budget" is essentially gone.) Stated another way, extra-column volumes and extra-column variances that are acceptable in the practice of conventional HPLC are generally inappropriate in the practice of capillary and nanoscale LC techniques. Capillary and nanoscale techniques are at the forefront of separations technology at this time, largely because of their suitability for interfacing with mass spectrometry, particularly where the available sample-mass for analysis is limited (sample-limited analysis.)

In practice, few if any manufacturers have demonstrated the ability to maintain separation efficiency across the orders-of-magnitude of characteristic peak volume recited in Table 1. Moreover, there is concurrently a trend toward the use of smaller packing particle size, to achieve yet-higher separation efficiency. This higher efficiency results in a further decrease in the volume of an eluting zone or band, further exacerbating problems with extra column effects. Planar fluid-circuit approaches to minimizing extra-column volume and extra-column variance seem appealing in their ability to consolidate function and produce relatively short routing paths, but to date the materials of construction (typically glass, plastics, or certain ceramics) have not permitted the devices to withstand the internal hydrostatic pressures typical of modern small-particle separations. These latter pressures may be in the range of 100 megapascals at the column head or higher, corresponding to regimes of UPLC™ or of very-high-pressure liquid chromatography (VHPLC.)

SUMMARY

In general, an aspect of the technology entails partially or fully integrated microfluidic circuits included in chemical-separation devices such as HPLC, UPLC™, VHPLC, super-critical fluid chromatography (SFC), or gas chromatography (GC) instruments; such circuits are advantageously fabricated, at least in part, from diffusion-bonded metallic layers having substantially similar compositions. In one embodiment, titanium substrates, of a great variety of thicknesses, are particularly well suited for fabrication and operation of such instruments. Some embodiments feature stainless steel diffusion-bonded sheets. In some exemplary embodiments of the technology, a chromatography instrument is fabricated, with various degrees of integration, from two or more diffusion-bonded metallic sheets. The two or more diffusion-bonded metallic sheets are joined to create a microfluidic device with a hermetically sealed interface between adjacent metallic sheets. At least one microfluidic channel, accessible by at least one of an inlet and/or an outlet is enclosed within the microfluidic device. Some embodiments entail preferred patterning methods and/or preferred surface modification methods for the wetted surfaces of the microfluidic channel. Some embodiments feature microfluidic channels packed with micrometer-sized particles serving as the stationary phase in a chromatographic separation. In addition, some embodiments include particle retaining elements in fluidic communication with the packed microfluidic channels. Some embodiments feature integrated electrospray tips to deliver fluids from the device.

In this application, the term microfluidic channel will be used to refer to a flow path feature typically suitable for supporting or sustaining capillary scale or nanoscale separations, where a characteristic transverse dimension of such channel will be typically in the range of tens to hundreds of micrometers.

In another aspect, the technology relates to a diffusion-bonded product manufactured including the steps of: (a) supplying two or more substantially compositionally similar metal sheets with each having a flat major surface with no layer introduced thereon to promote bonding; at least one of the two or more metal sheets including at least a portion of a microfluidic channel disposed therein; (b) bringing the flat major surfaces of each of the two or more metal sheets into a contacting relationship with at least one of the two or more sheets thereby forming an interface and forming and enclosing the microfluidic channel at the interface between such sheets, the microfluidic channel having at least one entrance port and at least one exit port; (c) heating the contacting sheets in a vacuum furnace or an inert-atmosphere furnace to a temperature substantially below melting temperature of such sheets; (d) urging the contacting sheets together under a compressive stress while the sheets are being heated to bond the sheets together by causing grains of the two or more metal sheets to merge across the interface from one sheet to the other sheet; (e) cooling the bonded two or more sheets to about room temperature; and (f) applying at least an organic coating to the microfluidic channel enclosed between the bonded two or more sheets through at least one of the at least one entrance port or the at least one exit port.

In this application, the term wetted surface will be used to identify any surface which will be in direct contact with a mobile phase fluid of a separation, during normal analytical operation or usage. This term distinguishes such surfaces from other surfaces of a structure which are not intended to be placed in contact with the mobile phase stream.

Some embodiments of this aspect of the technology include one or more of the following features. The diffusion-bonded product is manufactured to further include the step of surface treating wetted surfaces of the microfluidic channel with a vapor after cooling but before applying the organic coating. In some embodiments, the vapor deposits amorphous silicon on the wetted surfaces. In some embodiments, the vapor deposits a layer of an inorganic-oxide on the wetted surfaces. The two or more substantially compositionally similar metal sheets can be formed of substantially similar titanium alloys or pure or substantially pure titanium. In one embodiment, a first sheet of the two or more substantially compositionally similar metal sheets is formed of a commercially pure (CP) titanium sheet and a second sheet is formed of a sheet of a titanium 6AL-4V alloy. In some embodiments, the two or more substantially similar metal sheets are formed of austenitic stainless steels in the AISI 300 series. The organic coating can include a perfluorinated carbon compound. Alternatively or additionally, the organic coating can include a hydrocarbon compound. The organic coating can also be formed of an organic material that has a desired hydrophobicity or hydrophilicity. The desired hydrophobicity or hydrophilicity is typically selected to reduce or prevent analyte or sample interactions with the wetted surfaces during chromatographic separations.

In another aspect, the technology relates to a microfluidic device for separating a sample by chromatography. The device includes diffusion bonded metallic sheets, each metallic sheet having a substantially similar composition. The diffusion bonded metallic sheets are joined to create a hermetically sealed interface between each adjacent metallic sheet without the introduction of a secondary material and to enclose a separation channel within the diffusion bonded metallic sheets accessible by at least one of an inlet or an outlet. Wetted surfaces of the separation channel are coated with an organic material at least one monolayer thick and the separation channel is packed with micrometer-sized particles serving as a stationary phase for a chromatographic separation.

Embodiments of this aspect of the technology include one or more of the following features. The diffusion bonded metallic sheets are formed of substantially similar titanium alloys or titanium. In one embodiment, a first sheet of the diffusion bonded metallic sheets is formed of a commercially pure titanium and a second sheet, adjacent to the first sheet, is formed of a titanium 6AL-4V alloy. In another embodiment, the diffusion bonded metallic sheets are formed of austenitic stainless steels in the AISI 300 series. Some embodiments feature an amorphous silicon material or layer deposited between the wetted surfaces of the separation channel and the organic material. Some embodiments feature a deposited layer of inorganic-oxide between the wetted surfaces of the separation channel and the organic material. The organic material can be substantially hydrophobic. Alternatively, the organic material can be substantially hydrophilic. The device can further include or define an electrospray tip. The electrospray tip is in fluid communication with the separation channel. Some embodiments feature a particle retaining element in fluidic communication with the separation channel. The particle retaining element is positioned between the separation channel and the outlet to an exterior surface of the diffusion bonded metallic sheets.

In another aspect, the technology relates to a method of manufacturing a microfluidic device for chromatographic separation of a sample. The method includes: (a) patterning a first metallic sheet to define at least a portion of a fluidic channel by coating a surface of the first metallic sheet, selectively removing one or more portions of the coating to expose one or more areas of the surface of the sheet, at least partially immersing the first metallic sheet in an electrolyte; and applying a voltage difference between the first metallic sheet and a counter electrode to selectively remove material from the one or more exposed areas by anodic dissolution to form at least a portion of the fluidic channel within the first metallic sheet; (b) providing a second metallic sheet, which has a composition substantially similar to the first metallic sheet; and (c) diffusion bonding the first metallic sheet to the second metallic sheet to form a hermetically sealed interface having direct metal contact of the first and second metallic sheets to form and enclose the fluidic channel at least partially patterned in the first metallic sheet between the first and second metallic sheets at the interface.

Embodiments of this aspect of the technology include one or more of the following features. The coating applied to the first metallic sheet in the patterning step can be a polymeric photoresist. In another embodiment, the coating can be a titanium dioxide layer. The coating is selectively removed by a lithographic technique, which incorporates the use of a mask, or is maskless (i.e., selective removal by a laser).

Some embodiments of the method of this aspect of the technology further include coating a wetted surface of the fluidic channel formed by diffusion bonding the first and second metallic sheets with a material to provide surface modification of the fluidic channel. The material forming the coating can be formed of, at least in part, an organic material. The material forming the coating can be formed of, at least in part, an inorganic-oxide. The material forming the coating can be formed of, at least in part, silicon. The coating can be deposited by vapor deposition of one or more materials on the wetted surface.

Some embodiments of the method of this aspect of the technology can further include patterning the first metallic sheet to also include particle retention features in fluidic communication with the fluidic channel. The method can also include a step of packing the fluidic channel with a plurality of micrometer-sized particles to provide a stationary phase medium of the chromatographic separation. Some embodiments of the method include fabricating an end of the diffusion bonded first and second metallic sheet to form an electrospray tip in fluidic communication with the fluidic channel.

There are numerous advantages of aspects of the present technology including, but not limited to, the ability to economically fabricate a chromatographic device capable of withstanding high internal pressures, in particular the high pressures associated with modern small-particle chromatographic separations. In addition, some aspects of the present technology provide advantageous fabrication methods, which lend themselves for feasible use in commercial production. Further, methods and devices fabricated in accordance to one or more of the above aspects allow for the alignment and retention of microfluidic features in the fabricated devices. In addition, devices and methods in accordance with one or more aspects described herein provide more accurate chromatographic data due to reduced sample interaction with wetted surfaces of the devices.

BRIEF DESCRIPTION OF THE FIGURES

The advantages of the technology described above, together with further advantages may be better understood by referring to the following description taken in conjunction with the accompanying drawings. The drawings are not necessarily to scale; emphasis instead generally being placed upon illustrating the principles of the technology.

FIG. 3 is an expanded perspective view of a fluidic device in accordance with an aspect of the technology.

FIG. 4 is another expanded perspective view of a fluidic device in accordance with an aspect of the technology.

FIGS. 5A, 5B, and 5C are side views illustrating a method of fabricating a fit in fluidic communication with a separation channel in accordance with the present technology.

FIGS. 5D and 5E are sectional views taken along lines F-F and G-G in FIG. 5C, respectively.

FIGS. 6A and 6B are side views illustrating another method of fabricating a fit in fluidic communication with a separation channel in accordance with the present technology.

FIG. 6C is a sectional view taken along line H-H in FIG. 6B.

FIGS. 7A and 7B are side views illustrating another method of fabricating a fit in fluidic communication with a separation channel in accordance with the present technology.

FIGS. 7C and 7D are sectional views taken along lines I-I and J-J in FIG. 7B, respectively.

DESCRIPTION

Figure 1:
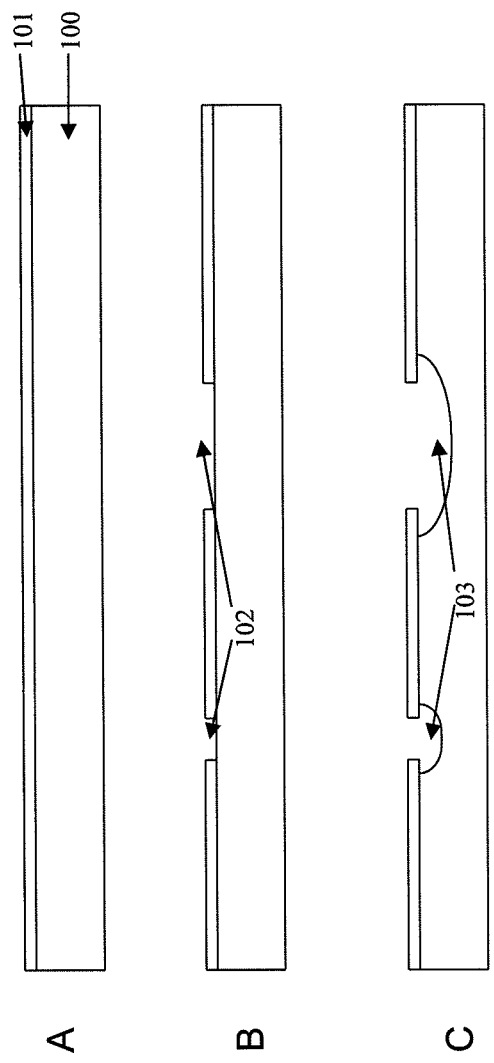
FIG. 1 is a cross-sectional view of a device at three different steps of a fabrication process in accordance with the present technology.

The following description, which includes descriptions of some embodiments that entail particular materials and fabrication steps, is intended to be illustrative rather than comprehensive. Accordingly, this description should be understood as not limiting devices and fabrication methods of the technology to any particular apparatus, materials, and process steps.

Diffusion bonding herein refers to elevated-temperature processing that leads to direct bonding of substantially metallic components. Generally, heat and compressive stress are used in combination to urge two or more components together. In advance of the bonding step, lapping and polishing processes are optionally used to achieve mating surfaces that are extremely flat (typically to within some 100's of nanometers,) and which have a surface roughness statistic $R_a$ under 250 nanometers and preferably under 50 nanometers.

Assuming that diffusion bonding of metals entails atomic-level contact at faying surfaces, elevated temperature and a modest compressive stress (for example, a 0.7 to 7.0 megapascals global-mean stress) appear to enable the necessary intimate contact, by yielding the localized surface asperities which would otherwise tend to hold the faying surfaces apart. Given time at temperature, grain boundaries of the parent materials re-distribute so as to substantially eliminate evidence of the original bond-line.

Extensive testing of mechanical test-specimens within the aerospace industry indicates that the bond lines formed in titanium and alloys such as Ti 6Al-4V substantially retain the strength and ductility of the parent materials. Titanium and alloys such as Ti 6Al-4V appear to be particularly well suited for vacuum diffusion bonding, as the base material appears readily capable of dissolving its own surface-oxide layer (passivation layer) at the bonding temperature. Thus one need not resort to unusual protocols in order to eliminate this passivation layer, and its effects upon the resulting bond. It will be recognized, however, that most metals can be diffusion bonded, when appropriate conditions are employed to deal with the passivation layer(s).

The diffusion bonding of like materials tends to produce a joint which is characterized by very low residual stress, which is in marked contrast to fusion welding techniques. In the diffusion bonding sequence for titanium, the faying surfaces are not taken to liquefaction. It is recognized that the temperatures involved (e.g., 840° C.) are sufficiently high to promote the yielding of local asperities. In most metals, an increase in temperature is commonly associated with a decrease in yield strength. As these local asperities respond to highly-localized stress by yielding, the resulting applied-stress value tends to converge with the global mean compressive stress value, which substantially terminates further yielding. When proper conditions are employed, the diffusion bonding of two or more titanium substrates should result in substantially no net change in the dimensions of the parts, once the parts are returned to ambient temperature. This is useful because machined details such as compression ports can be introduced in the components at the time of initial machining, and those details will remain substantially accurate and usable following the bonding process.

By way of introduction, some embodiments of the technology utilize two or more diffusion-bonded layers of metallic materials. "Diffusion bonding" in the context of the following embodiments is the application of heat and force onto two or more parts formed of substantially the same metal in such a manner that adjacent substantially flat major surfaces come into atomic contact with each other and that grains and/or grain boundaries adjacent to the interface between the two parts rearrange themselves in an attempt to achieve a lowest-energy conformation, with the ideal result that the bonded parts show no evidence of the original interface and that the bonded region has substantially the same strength as the bulk metal.

"Same metal" or "substantially same metal" refers here to metals which have substantially similar compositions. For example, a commercially pure titanium part can be bonded to another commercially pure titanium part, or a 300-series stainless steel part can be bonded to a 300-series stainless steel part (e.g., bonding 304 type to 304 type; bonding 316 type to 304 type), or a commercially pure titanium part can be bonded to a titanium alloy part, but a titanium part is not bonded to a stainless steel part. As a result, the same metal or substantially same metal has a substantially same composition as an adjacent diffusion-bonded sheet. Thus, the sheets may be defined as substantially compositionally similar metal sheets.

In embodiments described herein, the maximum bonding temperature is generally at a temperature substantially below the melting temperature of the parent metal. In some embodiments, the maximum bonding temperature is between 50% and 80% of the melting temperature. In certain embodiments, the maximum bonding temperature is about 90% of the melting temperature of the parent material. The bonding temperature is typically reached after a ramp-up lasting several hours, and that bonding temperature plateau is typically followed by a ramp-down to ambient temperature lasting several hours as well. The force (a compressive stress) applied to the parts during bonding is sought to be as small as possible so as to prevent deformation of internal features such as channels and holes. Typical bonding compressive stresses are in the range of 0.7 to 7.0 megapascals.

Diffusion bonding preferably utilizes heat, force, and a vacuum or inert atmosphere that is substantially free of oxygen. Diffusion bonding has significant advantages over alternative joining methods such as fusion welding or brazing. Fusion welding creates very high temperatures that may deform the fine machined features and may introduce residual stresses after cooling. Residual stresses are substantially absent from parts that are diffusion bonded in an appropriate manner. Brazing introduces a secondary material or interlayer between the bonded parts. While this makes joining possible at temperatures that are much lower than the melting temperature of metals, such as titanium or stainless steel, the strength of the bond is lower than that of the parent metals and the introduction of a different metal raises additional issues of sample contamination from the wetted surfaces and sample adsorption onto those surfaces. Moreover, the temporary liquefaction of the braze metal typically generates problems with unintended flow of braze into channels or other fine structures, causing blockages.

Diffusion bonding is performed in any suitable atmosphere or in vacuum. Some suitable atmospheres include inert gases, such as nitrogen, argon or helium. In some embodiments of the technology, associated with a planar fluid circuit, the strength, stiffness, ductility, and fracture-toughness of an appropriately-selected structural metal allows that metal to perform well in a planar fluid circuit implementation where more-brittle materials would risk rupture, as the metal is capable of responding locally to a stress concentration without propagating a fracture that could destroy the device integrity.

Metallic layers are composed of any suitable materials, including known metallic materials. One suitable class of structural metals having the strength, stiffness, corrosion resistance, ductility, and fracture-toughness necessary to implement some high-pressure fluid circuits is the class of titanium alloys (including substantially pure titanium.) For example, some suitable titanium materials are available from Allegheny Technologies Inc.'s AllVac Division (Monroe, N.C., USA). These materials include: ALLVAC® 30, 40, 55, and 70 CP (commercially pure) titanium grades, which have different yield strengths associated with different oxygen levels; and ALLVAC® titanium 6Al-4V and 6Al-4V ELI alloy (includes about 6.3% Al, 3.8% V, and 0.017% Fe.) Certain forms of titanium which are not intentionally alloyed may be sold under the designation CP (for "commercially pure".) During diffusion bonding of titanium layers, the titanium solubilizes its own oxide layer at a temperature under the bonding temperature.

The following description focuses on embodiments that include titanium diffusion-bonded components. Some principles of the technology are applicable, however, to diffusion-bonded components formed from other metals. The word "titanium" is used in the following to refer to both substantially pure titanium and suitable titanium alloys. Some preferred embodiments utilize iron-alloy bonded components, using, for example, stainless steels which are members of the AISI 300 series of Cr/Ni alloys, Members of the AISI 300 series, include, for example, type 316 surgical stainless steel, type 316L extra low carbon stainless steel, type 304, and type 304L. Stainless steel types 316 and 304 have similar mechanical properties but differ in molybdenum content at the level of a few percent. The increased molybdenum content of type 316 is considered to impart somewhat better overall corrosion resistance, along with improved resistance to pitting or crevice-corrosion, in the presence of chloride salts. While type 316 may exhibit better native corrosion resistance, devices described herein can be made from type 304 with substantially the same performance as devices formed from type 316, when appropriate surface modification is applied. Surface modification techniques and procedures are provided below.

Suitable methods of forming fluid paths in high-pressure titanium-based, or other metal-based, fluidic circuits include, for example, photochemical through-etching of thin sheets, or photochemical blind-etching of thicker sheets, of the metal material. Alternatively, the material removal required to generate fluid paths may be accomplished by electrochemical milling, laser ablation, laser ablation with oxygen gas feed, electrical discharge machining ("EDM"), focused ion beam ("FIB"), electron-beam cutting, reactive-ion dry etching, mechanical cutting, or any alternate suitable means. Some fabrication methods are described in more detail below.

A planar fluid path is optionally implemented substantially within a single through-etched thin layer or foil, which is optionally subsequently captured between two unetched facing layers. Alternatively, the fluid path may be implemented as a blind-etch in one material layer, or as mirror-image blind-etches constructed in two sheets of material which share a bond plane. If desired, a circuit could incorporate a fluid path which is through-etched in a central foil, in addition to blind-etched fluid path components residing in the facing sheets.

The fluid path may reside in a plurality of distinct layers, with vias used to interconnect between planes as desired, analogous to that found in printed circuit board (PCB) construction. The metal facing sheets may be constructed with machined features which permit high-pressure fluid-tight connections (for example, threaded compression ports) to be made to the bonded assembly, facilitating assimilation of the bonded assembly into realistic systems incorporating high-pressure pumps, sample injectors, detectors, etc., thereby overcoming one of the limitations of prior art planar fluid circuits implemented in other materials.

As a component of a high-pressure-capable separation system, a bonded titanium fluid-path element optionally is used to encompass or implement any portion of a system for which it is deemed suitable, including a separation column packed with a stationary-phase, an in-line heat exchanger, a detector cell or cell component, a pump manifold, and/or a component of a sample injector, for example. The complete functionality of a separation system need not reside on a single bonded device, but, rather, that functionality is optionally spread across multiple devices which have size- and internal-volume-scales, and circuit complexity, appropriate to their designated tasks.

Some appropriate methods of joining structural metals readily produce a high-pressure-capable, fluid-tight seal over the joining plane, without corrupting the fluid-path features lying within the joining plane, or immediately adjacent to it, and preferably without introducing or exposing secondary materials to the fluid path. Some examples of secondary materials are brazes (e.g., a nickel-gold braze) and melting-point depressants (e.g., a boron-based melting-point depressant). In the case of a braze, the braze material achieves melting or liquefaction at a temperature below the melting temperature of the parent materials. Even high-quality braze materials such as nickel-gold typically exhibit less chemical inertness than selected substrate materials such as 316 or 316L stainless steel. Melting-point depressants are a separate class of materials from brazes and contribute to metal-joining by causing a very thin superficial layer of the substrate to become molten at a temperature below the unadulterated melting temperature of the bulk substrate material. There is an identified class of metal joining procedures called transient-liquid phase (TLP) joining or bonding, the practice of which may incorporate the use of such depressants. Secondary materials are introduced materials, such as, for example, brazes and melting-point depressants, and do not include native oxide layers or other naturally-occurring materials.

As indicated above, titanium and titanium alloys are joined, for example, by vacuum diffusion bonding. Any suitable diffusion-bonding process, including known processes, is optionally employed. Some suitable vacuum diffusion-bonding processes are presently utilized in the aerospace industry. Vacuum diffusion bonding permits appropriately-prepared titanium surfaces to be directly bonded under prescribed conditions which include, for example, provision of a controlled atmosphere, elevated temperature, compressive stress on a laminate stack, and time; such conditions generally do not require the use of an intervening filler metal or braze (i.e., secondary materials). Vacuum diffusion bonding of titanium and titanium alloys generally provides an integral component, in which grain boundaries of adjoining layers and/or grain boundaries resident at or near the interface(s) between layers have migrated so as to span the original bond plane or planes. When properly designed, a plurality of layers is optionally bonded at one time, within the context of one vacuum-furnace "oven run".

As one example, the above-mentioned Ti-6AL-4V alloy is optionally diffusion bonded with a nominal mean compressive stress of about 0.7 to 7.0 megapascals and with heating applied over the course of multiple hours, typically with a shallow linear ramp of temperature employed from the room-temperature condition to the bonding temperature condition, and from the bonding temperature condition back down to room temperature. The maximum temperature reached during the bonding cycle is typically above 700° C. and under the beta transus temperature (e.g., 980° C. for Ti-6Al-4V.)

Preferably, the contacting layers have a good surface finish, for example, a surface roughness statistic $R_a$ under 250 nanometers and preferably under 50 nanometers. Bonding occurs in any suitable environment, such as an inert gas, or a vacuum of $1.0 \times 10-5$ torr or better. Preferably, the environment is substantially free of oxygen.

Diffusion bonding of a stacked assembly converts the stack to bonded state, forming a substantially monolithic structure in which the originally distinct metallic layers are often no longer individually distinguishable. That is, an interface between layers (also referred to as a bond-plane) is replaced with a grain structure typical of the bulk material, such that the original bond plane is no longer visible.

As was described above, many of the ease-of-use and reliability issues in a capillary-scale or nanoscale liquid chromatography (LC) system arise from the difficulty in making low dead-volume interconnections. A microfluidic-based LC system has the potential of avoiding many of these issues. At least some LC components are constructed as microfluidic elements, and desirable interconnections are made between these elements via suitable microfluidic channels.

As a component of a high-pressure-capable separation system, a diffusion-bonded titanium fluid-path element optionally is used to encompass or implement any portion of a system for which it is deemed suitable, including a particulate-packed separation column and/or other component(s). The complete functionality of a separation system need not reside on a single bonded device, but, rather, that functionality is optionally spread across multiple devices which have size- and internal-volume-scales, and circuit complexity, appropriate to their designated tasks.

As described above, some planar devices, referred to herein as microfluidic devices, support HPLC, UPLC™, and ultra-high-pressure liquid chromatography (UHPLC) to permit separation of small volumes of samples with reduced connection-count and dead volume between hydraulic components of the device and therefore improved performance and robustness. HPLC separations are commonly conducted at pressures up to approximately 35 megapascals. Some optional materials, for microfluidic applications, such as glass, silicon, and polymers, generally cannot withstand an internal pressure of 35 megapascals, but may break, for example, either through brittle failure in the case of silicon and glass or delamination in the case of polymers. Moreover, embodiments of the technology support separations at even higher pressures, up to 135 megapascals or even higher.

Some embodiments of the technology are planar devices for elevated-pressure chromatography applications, fabricated from metals using primarily electrochemical micromachining (EMM) and diffusion bonding. While the metal used to fabricate the device is unlimited, some illustrative examples are titanium, preferably ASTM Grade 1, 2, 3, 4 or 5 titanium, and AISI 300-series stainless steel. For example, sheets of titanium or stainless steel, of thickness 50 micrometers to 500 micrometers, are first polished so that their surface roughness $R_a$ is less than about 250 nanometers to create flat major surfaces. Geometric features, such as channels, inlet and outlet holes, and alignment holes, are machined in these sheets using techniques especially suited for producing appropriate-quality surface finishes, such as, as described in part above, electrochemical micromachining (EMM) for in-plane channels. Electrical discharge machining (EDM), and picosecond laser machining are optionally used to form features where the surface finish is somewhat less critical.

The sheets are then joined using diffusion bonding to form hermetically-sealed devices capable of withstanding internal hydraulic pressures in excess of 135 megapascals as well as large external forces and bending moments. In addition, some embodiments utilize surface modification of wetted surfaces to isolate the sample analytes from, for example, titanium and/or stainless steel metallic walls and prevent sample adsorption onto the walls or metal leaching into the sample. This provides a solution for two possible problems: 1) selection of the material(s) best suited for fabrication, and 2) interaction of the sample analytes with this material(s).

In some approaches, microfluidic channels and holes in metallic substrates have been formed by wet chemical etching, excimer laser ablation, and mechanical milling and drilling; these techniques can produce rough surfaces that are not suitable for certain liquid chromatography applications. Another optional technique to machine features in titanium is deep reactive ion etching (DRIE). While DRIE can produce highly-accurate features with good surface finish, it may be slow and require expensive fabrication tools in a clean-room environment.

Electrochemical micromachining (EMM), derived from electrochemical machining (ECM), is suitable for producing high-quality surfaces with tight tolerances in metals. In ECM, the workpiece to be machined is made the anode of an electrolytic cell containing an electrolyte. The tool is made the cathode, and in one optional mode, the cathode shape may be the negative of the shape to be imparted to the workpiece. By application of a voltage between the workpiece and the tool, metal atoms are anodically sacrificed from the workpiece and are converted to liquid-phase ions, which are solvated and transported away by the electrolyte solution. Moving the tool toward the workpiece may impart to the workpiece a desired shape, which can be arbitrary and three-dimensional.

As noted, EMM is a variant of ECM, and is optionally used to machine planar devices. One version of a technique, according to one embodiment of the technology, is illustrated in FIG. 1, which shows the cross-section of a device at three different steps (labeled A, B, and C in FIG. 1) of the fabrication process. A photoresist layer 101 is applied over the metal substrate 100, for example using spin-coating. Openings 102 in the photoresist layer are defined by photolithography. The part is made the anode of a three-electrode electrolytic cell and is immersed in an electrolyte such that only the top surface is exposed to the electrolyte. The electrolytic cell additionally contains a cathode and a reference electrode located away from the part. An electric field is applied between the part and the cathode. Electrical current flows from the cathode to the part. Metal atoms are removed from the part ("anodic dissolution") and form liquid-phase ions that are removed by gentle agitation of the electrolyte. The reference electrode serves to stabilize the applied voltages.

Material is removed by anodic dissolution only from the open regions of the photoresist layer, resulting in cavities 103. Material is removed in the vertical direction but also horizontal direction so that the cavities are rounded. The width and depth of the cavities depends on the width of the openings 102 in the photoresist layer 101 and on the amount of electrical charge or current delivered by the power supply, called the potentiostat. One may control the cross-sectional dimensions of the cavity to within a few micrometers or better. The accuracy of the location of the cavities is substantially determined by the accuracy of photolithography, which can depend on the accuracy of the mask, but positional accuracies of a few micrometers, certainly less than 10 micrometers, can be achieved.

More generally, EMM is also called "electroetching" or "electrochemical micromachining through a photomask," and is only superficially similar to a wet chemical etching process called "photochemical machining" (PCM), which is commonly used in the electronics industry. Material removal in PCM is due to chemical attack of the metal substrate by a chemical etchant, whereas it is due to electrochemical/anodic dissolution in EMM.

PCM typically provides smooth etched surfaces in silicon or glass but very rough surfaces in metals because the acid etchant tends to attack grain boundaries (i.e., "intergranular attack".) In the latter case, the resulting etched sidewall surfaces are typically not smoother than the characteristic grain size of the metal substrate. This makes PCM not well-suited for certain applications in chromatography where very smooth channel sidewalls are desired. For example, such channels might eventually be filled with stationary-phase particles having a diameter between 1 and 5 micrometers, in a process referred to as "packing", so as to serve as chromatographic separation column. Producing a packed bed that is dense and uniform is critical to achieving good chromatographic performance. A channel with smooth sidewalls is preferable to support better packing than a channel with rough sidewalls, and therefore provide better chromatographic performance.

Under certain conditions involving high applied voltage, low electrolyte and substrate temperature, EMM can lead to extremely smooth surfaces, referred to as "surface brightening", a phenomenon also commonly used in electropolishing for a finishing applications of metallic parts.

Figure 2:
FIG. 2 is a cross-sectional view of a titanium sheet in which two channels with different widths and depths have been fabricated using a method in accordance with an aspect of the present technology.

FIG. 2 shows the top of a titanium sheet in which two channels 200 and 201 with different widths and depths have been fabricated using EMM. The cross-sections of both channels are approximately semi-elliptical. The sidewalls machined by EMM are very smooth, with average surface roughness as low as 25 nanometers. In a variation of the process described in FIG. 1 that is specific to titanium, the polymeric photoresist layer 101, whose thickness is generally greater than 1 micrometer, can be replaced with a titanium oxide layer of thickness 50-300 nanometers. The oxide layer is then selectively removed in a maskless lithographic technique in which an excimer laser removes targeted material.

Because of the isotropic nature of the material removal process, EMM is not suited to making vertical holes through metal sheets of thickness 50-500 micrometers. Instead, some embodiments use one of several other techniques: electrical discharge machining (EDM), picosecond laser machining, or mechanical drilling. Inlet and outlet port holes are preferably of diameter 50-300 micrometers and should have smooth sidewalls since they are part of the fluid path and might be packed like the separation channel. Alignment holes can be much larger and do not require smooth sidewalls. EDM and picosecond laser machining can be used to make holes of diameter smaller than 100 micrometers with good surface finish and without the need for secondary finishing operations. Mechanical drilling can be used to make holes of diameter larger than 100 micrometers but a finishing operation such as deburring might be required and is undesirable. Note that all three techniques could be used to make channels as well as holes but it is unlikely that the channel sidewalls would be as smooth as those obtained with EMM.

After channels and holes have been machined, the metal sheets are stacked and aligned typically using alignment holes, and then joined using diffusion bonding to form monolithic parts with hermetically sealed internal channels. The internal channels can be microfluidic channels used to conduct chromatographic separations (i.e., separation channels). The internal channels are accessible by at least an inlet and/or an outlet. In some embodiments, the internal channel is accessible by multiple inlets and/or multiple outlets. In some embodiments, the inlets and outlets are formed (e.g., drilled) in the flat major surfaces of the metal sheets. In other embodiments, the inlets and/or outlets are positioned at the interface of two adjacent sheets at an exterior edge of the device.

Referring to FIG. 3, a microfluidic device includes two metal sheets or layers. The top layer 300 contains holes 302, 303, 304, 305, 306, 307, and 308 and slot 309 made by micro-EDM, wire EDM, mechanical drilling, or laser drilling. Holes 302 and 303 have diameter 50-300 micrometers and are used as fluidic access ports or vias. Holes 304, 305, 306, and 307 are used to attach a fitting at an exterior edge 310 of the device so as to provide fluidic access on the edge or side 310 of the device. Bottom layer 301 contains two grooves 311 and 312 of depth less than the thickness of the layer 301, made by EMM or milling, holes 315, 316, 317, 318, and 319 and slot 320. In an embodiment where EMM is used to make the grooves 311 and 312, groves 311 and 312 correspond, respectively, to channels 200 and 201 of FIG. 2 and have an approximately semi-elliptical cross-section. Whether EMM or milling is used to make the grooves 311 and 312, a high degree of surface smoothness is sought. An average roughness $R_a$ of less than 250 nanometers is desirable and less than 50 nanometers is preferable.

After machining of all grooves and holes, the bottom surface of the top layer 300 and the top surface of the bottom layer 301 are placed in contact and aligned using fixing pins inserted in holes 308 and 319 and slots 309 and 320. The stacked layers 300 and 301 are diffusion-bonded so that the grooves 311 and 312 become fluidic channels (e.g., separation channels) capable of holding fluids hermetically under high hydraulic pressures. The beginning of the channel 311 is at 313 and is located under the hole 302. Channel 311 mates with channel 312 at 314, which is located under hole 303. Holes 302 and 303 thus define fluidic vias or access ports (e.g., inlets) to channels 311 and 312. Additionally, a channel may extend to the edge (e.g., 310) of the bonded part, defining another fluidic access port, as is shown at 321. The cross-sections of the channels have semi-circular or semi-elliptical shapes when EMM is used, with typical axes lengths of 50-500 micrometers and rectangular shapes when milling is used, with typical width and height of 50-500 micrometers.

It is understood that layer 300 can consist of two or more identical sheets or foils of metal processed in the same manner.

In another embodiment, shown in FIG. 4, a microfluidic device includes three metal sheets or layers and all features are made by EDM. Top layer 400 is identical to the top layer 300 of the first embodiment and contains the small vias 403, which are made by micro-EDM, wire EDM, mechanical drilling or laser drilling. Middle layer 401 contains slots 404 and 405, which are cut through the entire layer and are made by wire EDM in such a manner that the sidewalls have surface roughness lower than 400 nanometers, and preferably lower than 200 nanometers. Top layer 400, middle layer 401, and bottom layer 402 also contain other features that are made by conventional wire EDM, such as the holes 410, 411 and 412 and slots 413, 414, and 415 used to align the three sheets prior to diffusion bonding. The bonded part creates hermetically sealed fluid passages or channels 405 and 406 in contact with the outside environment through ports 403 and 406. The cross-section of the channels is rectangular, with height defined by the thickness of the middle layer, unlike the rounded cavities 103 of FIG. 1. Typical heights and widths of channels 405 and 406 are 50-500 micrometers.

After fabrication and bonding, the channels 404 and 405 are packed with micrometer-sized particles, which will serve as the stationary phase in chromatographic separation. (It should be noted that formed channels 311 and 312 of the embodiment shown in FIG. 3 can also be packed with micrometer-sized particles for a chromatographic separation.) It is preferable to provide a means of preventing the particles from escaping the channels when liquid flows through the channel. For example, a retaining structure, or frit, is optionally created at the end of a column, for example by sintering the particles in a small region, or by dipping the end of the column in a polymer solution and curing the polymer to lock the particles in place. Additionally, EMM can be used in a variation of the first embodiment to create mechanical features in bottom layer 301 that act as retaining structures. Generally, such a particle retention element may be termed a weir. Three embodiments of particle retention elements or features made by EMM are shown in FIGS. 5, 6, and 7 and are described next.

In a first embodiment (shown in FIGS. 5A-5E), the channel that is to be packed terminates into a narrower channel that creates a restriction at which particles will be retained. A first photolithographic operation creates mask opening 500 (FIG. 5A). Electroetching through this opening creates channel 501, also shown in cross-section in 505 (FIG. 5D). A second photolithographic operation (FIG. 5B) creates a narrower mask opening 502. Electroetching through this opening creates narrow channel 503, also shown in cross-section in 506 (FIG. 5E). The shape and size of the two channels are determined by the width of the mask opening defined by photolithography and by the amount of electrical charge provided to the electrolytic cell by the electrical power supply. The depth of channel 506 can be made as small as 1 micrometer and can thus be a physical barrier for micrometer-size particles. However, such a shallow flow passage can easily be clogged by debris or precipitates from the solution. Alternatively and to prevent flow blockage, channel 506 can be given a slightly larger depth of between 5 and 10 micrometers. Particles of size 1.5-5 micrometer will "bridge", or lock themselves in place when they transition between the channel 501 and the narrow channel 503, effectively forming a retaining structure for the packed bed.

In a second embodiment (shown in FIGS. 6A-6C), a mask opening 601 for the narrow channel is shifted slightly relative to the channel 600 by a small distance 602 (FIG. 6A). If this distance is determined appropriately, a neck 604 is created between channels 600 and 603 by electroetching through mask opening 602 (FIG. 6B). The gap between the top plane 605 of the metal sheet and the top of the neck 606 is ideally between 1 and 5 micrometers (FIG. 6C).

In the third embodiment (shown in FIGS. 7A-7D), after the channel to be packed 700 is first made, with cross-section as seen in 705 (in FIG. 7C), a second photolithography operation creates a pattern 701 (FIG. 7A). The dotted area represents the open part of the mask (FIG. 7A), which is electroetched to form a shallow region 703 of depth 1-5 micrometers (FIG. 7B). The masked features 702 result in weir structures 704, which act as retaining structures for the particles. The plurality of weirs 704 reduces the risk of clogging or flow blockage. A cross-sectional view of weirs 704 is shown in FIG. 7D.

The outlet of a chromatographic separation column may be directed to the inlet of a mass spectrometer for analysis, a common technique for ionization of the liquid sample being the formation of a Taylor cone at the tip of electrospray nozzle, also commonly referred to as electrospray tip or emitter. In the case of planar microfluidic chromatographic devices, external, such as commercially available, electrospray emitters may be connected to the outlet of the separation channel using high-quality, low dead volume fluidic seals.

Figure 8A:
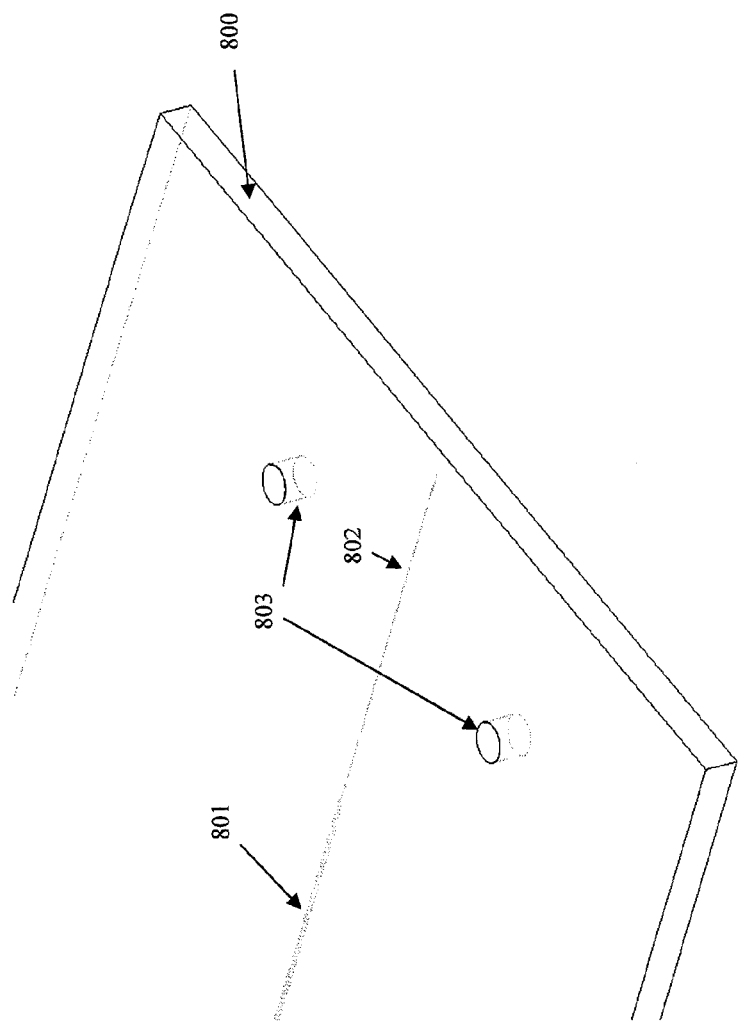
FIGS. 8A-8C are perspective views showing the fabrication of an electrospray tip on an end of a fluidic device.
Figure 8B:
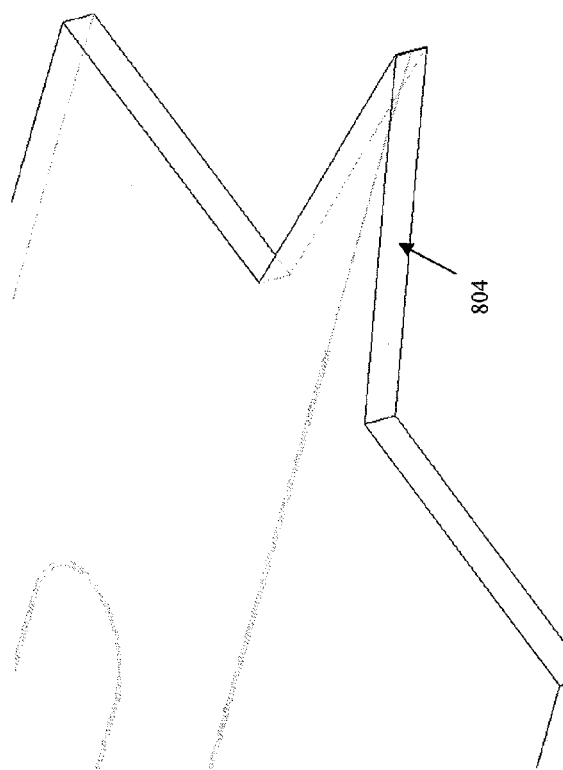

Alternatively, some embodiments include an electrospray emitter as an integral part of the device. An illustrative metallic device, according to one embodiment of the technology, includes an integrated electrospray tip made using EMM and EDM (FIG. 8A-D). Device 800 contains the separation channel 801, which is packed with chromatographic particles, and a narrower channel 802, which is not packed. (See, FIG. 8A). An EDM wire is aligned accurately to the device 800 through use of registration holes 803, or other registration features known to those of skill in the art (FIG. 8A). This EDM wire is used to cut the tip 804 (FIG. 8B).

Figure 8D:
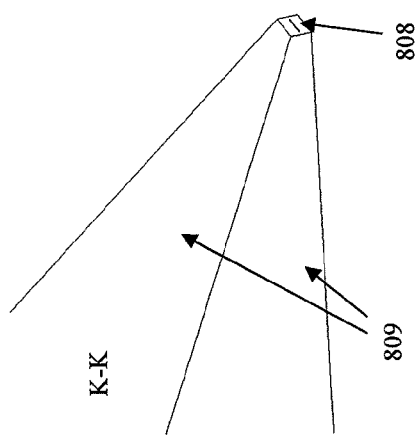
FIG. 8D is a close-up perspective view of area K-K indicated in FIG. 8C.
Figure 8C:
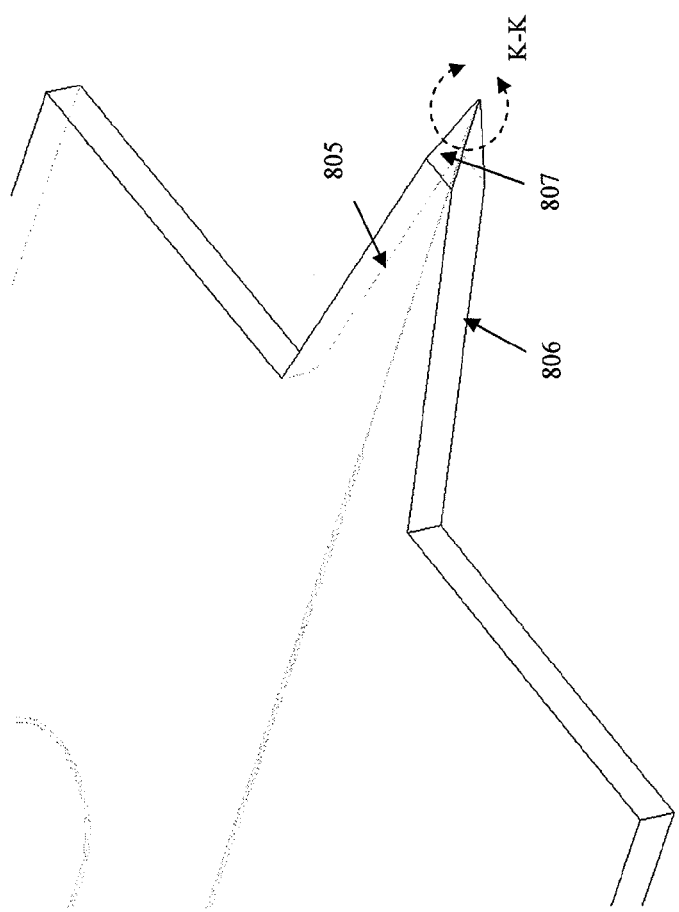

The device 800 is then rotated and the EDM wire is aligned to the top surface 805 and bottom surface 806 (FIG. 8C) prior to cutting the tip 807. The end of the tip is shown in detail K-K (FIG. 8D). The goal is for the tip end 808 to be as small as possible so that fluid delivered by channel 802 remains confined to tip end 808 and does not spread to the other surfaces 809 of the tip. It will be apparent to those of skill in the art that EDM cutting is an appropriate technique for making very small and therefore mechanically fragile tips since it does not involve mechanical contact with the machined part during machining.

The tip end 808 is rectangular in this embodiment. Alternatively, the tip 807 may be electrochemically machined to produce a rounded tip 807 and hence a circular tip end 808. In another alternative embodiment, the device 800 may be rotated during wire EDM cutting to produce a rounded tip 807.

Surface Behaviors and Surface Modifications

As the volume-scale of separation decreases, the surface-area-to-volume-ratio of the fluid system rises. A large change in volume-scale (for example, from conventional-scale LC to capillary scale or nanoscale LC) implies a concomitantly large change in the surface-area-to-volume-ratio which is characteristic of the analytical stream and the containing device(s).

Particularly when biomolecules are being manipulated for separation and analysis, this dramatic increase in surface-area-to-volume-ratio can become very problematic in practice, due to the many, and varied, modes of interaction which biomolecules (for example, proteins, peptides, carbohydrates, lipids, and combinations thereof) can have with surfaces. However, all analytes have the potential to interact with surfaces, and if the degree of interaction varies across a group of analytes, such interactions can produce highly undesirable biases in the analytical results.

A specific example is the following. Titanium and certain of its alloys are considered to be relatively chemically-inert metal materials, and, as a consequence, are used within the chemical processing industry where aggressively-corrosive conditions may be encountered. The typical chemical "passivity" of titanium arises from the presence of an oxide layer ("passivation layer") of $TiO_2$ which forms spontaneously on the surface of the metal when oxygen is available in the environment adjacent to the metal surface.

Chemical passivity is generally retained under conditions where the oxide layer can be maintained (and typically is lost under conditions where the oxide layer cannot persist, and/or cannot self-repair.) The term "chemical passivity" as employed above refers to the relative absence of corrosive degradation and leaching (more generally, the sacrificing) observed with the metal in the presence of an aggressive chemical environment.

However, the $TiO_2$ passivation layer exhibits a marked tendency to bind phosphopeptide compounds, and while this binding does not degrade the underlying metal per se, it certainly biases an analytical result where phosphopeptides comprise one of several (or one of many) classes of peptides which are undergoing analysis. Complete loss of the phosphopeptides as a compound-class is demonstrable in the context of a nanoseparation. $TiO_2$ in a microparticulate or nanoparticulate configuration (which may be referred to as titanium dioxide pigment) actually finds use in bioanalysis when one wishes to selectively and knowingly pull-down phosphopeptides from a mixture.

That the walls of a nanoseparation device can give rise to essentially complete loss (through binding) of the phosphopeptide component of an analytical mixture, is a statement of the extent to which the surface-area-to-volume-ratio is large in microfluidic devices. This inadvertent loss of phosphopeptides, as a compound-class, from an analytical result, is unacceptable in an instrument where qualitative and quantitative analysis of peptides is being undertaken.

Therefore, one recognizes that a suitable material-of-construction for capillary and nanoscale separation devices must satisfy a number of very different requirements, among which is a minimal degree of interaction at wetted-surfaces with the analytes which are targeted for separation and analysis. Thus, some embodiments of the technology utilize surface modification of wetted-surfaces as part of a "divide-and-conquer" approach, where materials-of-construction that are structurally suitable, and that lend themselves to patterning and bonding, are surface-modified to satisfy the above-described requirement of minimal interaction with analytes. Surface modification may also play a role in further reducing corrosive attack of certain metals (such as iron leaching observed from stainless steels) which can complicate or invalidate analytical results (separate from analyte binding.)

According to various embodiments, surface modification takes any of a number of forms. Two examples are discussed below.

Surface-modification, according to one embodiment, uses gaseous-phase precursors applied to an otherwise fully-fabricated planar fluid circuit, prior to any particulate packing of such device. The gaseous-phase enters a channel enclosed within the device (i.e., a fully-fabricated planar fluid circuit) through at least one of an inlet or an outlet to the channel. In some embodiments, the gaseous-phase enters through multiple inlets or multiple outlets. In certain embodiments, the gaseous-phase enters through both the inlet and the outlet. The gaseous-phase forms a material that deposits along the wetted surfaces of the channel. If necessary, the surfaces of a microfluidic device are first chemically cleaned (liquid-phase solvent cleaning, for example, or inorganic acid cleaning) to eliminate loosely-adhering contaminant overlayers (most typically of hydrocarbon contaminants derived from the surrounding air) which might interfere with the bonding of the intended, introduced surface. A final cleaning step is preferably performed with an oxygen plasma, with this step occurring directly within the processing chamber immediately prior to the intended deposition steps. In this way, the substrate is not exposed to atmosphere, even briefly, between the oxygen plasma processing and the deposition processing.

In an embodiment, the first deposition is a chemical vapor deposition ("CVD") inorganic oxide, typically $SiO_2$, which provides a reactable foundation for subsequent deposition of an organic overlayer. That foundation may correspond to multiple monolayers of depth. The CVD oxide process leaves behind a surface to which an organic (hydrocarbon, or potentially fluorocarbon) material can be covalently bound (this phase optionally includes, for example, a C8 or C10 aliphatic hydrocarbon chain.)

In one embodiment, the $SiO_2$ material is created by exposing an amorphous silicon deposit to oxygen or oxygen and heat. In this embodiment, a portion of the amorphous silicon deposit is oxidized.

In another embodiment, a layer of amorphous silicon is deposited prior to the deposition of an organic material.

Prior to the deposition of the organic material, but after the fabrication of the microfluidic channels within a diffusion-bonded device, the device is cooled to about room temperature ($\pm 5°$ C.) Typically cooling is carried out by a ramp-down of the vacuum or inert atmosphere furnace followed by removing the device from the furnace and leaving the device at atmospheric/room temperature for a period of time. In embodiments of the present technology, the device can be cooled more rapidly within the furnace by turning off power to the heating elements with or without activating fans or additional cooling means connected to the furnace to cool the device at a specified rate. In any event, the device is cooled to about room temperature prior to depositing the organic material on wetted surfaces of the microfluidic channel.

At temperatures well above room temperature (e.g., 400° C. and above), organic materials can burn off, and as a result if the wetted surfaces are at too high of a temperature the organic material will not coat or will not coat evenly on these wetted surfaces. To obtain a uniform coating, the device is cooled to about room temperature prior to deposition.

The organic material or in some embodiments organic overlayer actually comprises a "bonded phase" in the parlance of liquid chromatography, interposed between the device material or substrate, and the solvated analyte(s) within the mobile-phase stream. The presence of this bonded phase is intended to mask direct interaction between the analyte and the native substrate. The hydrophobicity or hydrophilicity of this bonded phase can be tuned by judicious selection of the organic functionality, or by the mix of organic functionalities, present.

An excessively hydrophobic surface can be deleterious if analyte becomes immobilized due to hydrophobic interaction with the phase. In that case, an undesirable "binding" behavior can still be observed, although the mechanism of binding may be different from that exhibited by the native substrate. Hydrophobic interactions can typically be "released" by assertion of a higher-percent-organic mobile phase composition (more strongly-solvating,) using the same principles exploited in reversed-phase chromatography.

The above surface-modification process is optionally performed with suitable commercially available equipment. For example, MVD® deposition tools available from Applied MicroStructures Inc. (San Jose, Calif., USA), typically sold for wafer-based material formats, are suitable for some deposition processes.

Various embodiments solve various problems associated with existing apparatus and methods. For example, some metallic microfluidic devices provide two key features: 1) the ability to withstand high pressures typical of HPLC, UPLC™, and VHPLC; and 2) internal channels with highly accurate dimensions and locations and very smooth channel walls, and/or passivated internal surfaces.

Some polymeric microfluidic devices are not capable of operation at internal pressures above about 35 megapascals. Some ceramic microfluidic devices, though capable of operating at pressures above 35 megapascals are brittle and may fracture when loaded in tension or bending, and their internal channels may have significant wall surface roughness, of the same order of magnitude as the particles they are packed with. Titanium-based microfluidic devices can be made using reactive ion etching (RIE), a dry etching technique common in semiconductor and MEMS (microelectromechanical systems) applications. RIE is capable of producing highly accurate and smooth features but requires very expensive equipment and is a very slow process, which impairs its economic feasibility for applications as HPLC/UPLC™/VHPLC/SFC consumables (columns). RIE is also generally not applicable to stainless-steel structures.

Various embodiments are optionally implemented for a variety of applications, such as HPLC/UPLC/SFC consumables, having channel cross-sections with equivalent diameters between 50 and 500 micrometers.

What is claimed is:

1. A microfluidic device for separating a sample by chromatography, the microfluidic device comprising:
   diffusion bonded metallic sheets, each metallic sheet having a substantially similar composition, the diffusion bonded metallic sheets joined to create a hermetically sealed interface between each adjacent metallic sheet without the introduction of a secondary material and to enclose a separation channel within the diffusion bonded metallic sheets accessible by at least one of an inlet or an outlet to the separation channel;
   wetted surfaces of the separation channel coated with an organic material at least one monolayer thick, a deposited layer of inorganic-oxide positioned between the wetted surfaces of the separation channel and the organic material, and the coated separation channel packed with micrometer-sized particles serving as a stationary phase in a chromatographic separation.

2. The device of claim 1, wherein the diffusion bonded metallic sheets comprise substantially similar titanium alloys or titanium.

3. The device of claim 2, wherein a first sheet of the diffusion bonded metallic sheets comprises a commercially pure titanium sheet and a second sheet of the diffusion bonded metallic sheets, which is adjacent to the first sheet, comprises a sheet of a titanium 6AL-4V alloy.

4. The device of claim 1, wherein the diffusion bonded metallic sheets comprise austenitic stainless steels in AISI 300 series.

5. The device of claim 1, wherein the organic material is hydrophobic.

6. The device of claim 1, wherein the organic material is hydrophilic.

7. The device of claim 1, wherein the diffusion bonded metallic sheets define an electrospray tip, the electrospray tip is in fluidic communication with the separation channel.

8. The device of claim 1, further comprising a particle retaining element in fluidic communication with the separation channel and positioned between the separation channel and the outlet to an exterior surface of the diffusion bonded metallic sheets.

9. A microfluidic device for separating a sample by chromatography, the microfluidic device comprising:
   diffusion bonded metallic sheets, each metallic sheet having a substantially similar composition, the diffusion bonded metallic sheets joined to create a hermetically sealed interface between each adjacent metallic sheet without the introduction of a secondary material and to enclose a separation channel within the diffusion bonded metallic sheets accessible by at least one of an inlet or an outlet to the separation channel;
   wetted surfaces of the separation channel coated with an organic material at least one monolayer thick, a deposited amorphous silicon material positioned between the wetted surfaces of the separation channel and the organic material, and the coated separation channel packed with micrometer-sized particles serving as a stationary phase in a chromatographic separation.

10. The device of claim 9, wherein the diffusion bonded metallic sheets comprise substantially similar titanium alloys or titanium.

11. The device of claim 10, wherein a first sheet of the diffusion bonded metallic sheets comprises a commercially pure titanium sheet and a second sheet of the diffusion bonded metallic sheets, which is adjacent to the first sheet, comprises a sheet of a titanium 6AL-4V alloy.

12. The device of claim 9, wherein the diffusion bonded metallic sheets comprise austenitic stainless steels in AISI 300 series.

13. The device of claim 9, wherein the organic material is hydrophobic.

14. The device of claim 9, wherein the organic material is hydrophilic.

15. The device of claim 9, wherein the diffusion bonded metallic sheets define an electrospray tip, the electrospray tip is in fluidic communication with the separation channel.

16. The device of claim 9, further comprising a particle retaining element in fluidic communication with the separation channel and positioned between the separation channel and the outlet to an exterior surface of the diffusion bonded metallic sheets.

* * * * *